(12) United States Patent
Delcroix et al.

(10) Patent No.: US 10,125,070 B2
(45) Date of Patent: Nov. 13, 2018

(54) PROCESS FOR THE TRANSFORMATION OF LIGNOCELLULOSIC BIOMASS INTO MONO- OR POLY-OXYGENATED MOLECULES

(71) Applicant: IFP Energies nouvelles, Rueil-Malmaison (FR)

(72) Inventors: Damien Delcroix, Saint-Maurice-l'Exil (FR); Christophe Vallee, Sassenage (FR); Amandine Cabiac, Givors (FR); Emmanuelle Guillon, Vourles (FR)

(73) Assignee: IFP EMERGIES NOUVELLES, Rueil-Malmaison (FR)

( * ) Notice: Subject to any disclaimer, the term of this patent is extended or adjusted under 35 U.S.C. 154(b) by 278 days.

(21) Appl. No.: 14/783,148

(22) PCT Filed: Apr. 7, 2014

(86) PCT No.: PCT/FR2014/050831
§ 371 (c)(1),
(2) Date: Oct. 8, 2015

(87) PCT Pub. No.: WO2014/167233
PCT Pub. Date: Oct. 16, 2014

(65) Prior Publication Data
US 2016/0060194 A1    Mar. 3, 2016

(30) Foreign Application Priority Data

Apr. 9, 2013   (FR) ..................... 13 53198

(51) Int. Cl.
| | |
|---|---|
| *C07C 31/18* | (2006.01) |
| *C07C 29/00* | (2006.01) |
| *C07G 1/00* | (2011.01) |
| *C08H 7/00* | (2011.01) |
| *C08H 8/00* | (2010.01) |
| *C08B 15/00* | (2006.01) |

(52) U.S. Cl.
CPC ............... *C07C 29/00* (2013.01); *C07G 1/00* (2013.01); *C08B 15/00* (2013.01); *C08H 6/00* (2013.01); *C08H 8/00* (2013.01)

(58) Field of Classification Search
USPC ......................................................... 568/852
See application file for complete search history.

(56) References Cited

U.S. PATENT DOCUMENTS

2011/0313208 A1    12/2011  Kalnes et al.
2013/0036660 A1*   2/2013  Woods .................... C10G 3/42
                                                              44/307

OTHER PUBLICATIONS

Vasllakos et.al. Ind. Eng. Chem. Process Des. Dev. 1984, 23, 755-763.*
International Search Report dated Sep. 9, 2014 issued in corresponding PCT/FR2014/050831 application (pp. 1-2).
Z. Tai et al., "Temperature-Controlled Phase-Transfer Catalysis for Ethylene Glycol Production from Cellulose", Chemical Communications, vol. 48, No. 56 (Jan. 1, 2012) pp. 7052-7054.

* cited by examiner

*Primary Examiner* — Ana Z Muresan
(74) *Attorney, Agent, or Firm* — Millen, White, Zelano, Branigan, P.C.

(57) ABSTRACT

The invention concerns a process for the transformation of lignocellulosic biomass or cellulose into mono- or poly-oxygenated compounds, in which the lignocellulosic biomass or the cellulose is brought into simultaneous contact with a catalytic system comprising a combination of one or more homogeneous catalysts and one or more heterogeneous catalysts, in the same reaction chamber, in the presence of at least one solvent, said solvent being water alone or as a mixture with at least one other solvent, in a reducing atmosphere, and at a temperature in the range 80° C. to 250° C. and at a pressure in the range 0.5 MPa to 20 MPa.

16 Claims, No Drawings

PROCESS FOR THE TRANSFORMATION OF LIGNOCELLULOSIC BIOMASS INTO MONO- OR POLY-OXYGENATED MOLECULES

FIELD OF THE INVENTION

The invention relates to a process for the transformation of lignocellulosic biomass or cellulose employing the simultaneous use of an original combination of one or more homogeneous catalysts and one or more heterogeneous catalysts. Using these catalysts means that upgradable mono- or poly-oxygenated products can be obtained directly and the formation of non-upgradable products can be limited. The term "non-upgradable" products means soluble and insoluble humins, i.e. high molecular weight products obtained from unwanted condensation reactions of sugars and their derivatives.

PRIOR ART

For a number of years, there has been a significant upturn in interest in incorporating renewable products into fuel and chemical sectors as a supplement to or substitution for fossil products. One possible route is the conversion of the cellulose contained in the lignocellulosic biomass into chemical products or intermediates, such as products containing one to six hydroxyl functions, n-propanol, ethylene glycol, propylene glycol, glycerol, 1,2-butanediol or 1,2-hexanediol.

The term "lignocellulosic biomass" (LCB) or lignocellulose encompasses several products present in quantities which vary as a function of their origin: cellulose, hemicellulose and lignin. Hemicellulose and cellulose constitute the carbohydrate portion of the lignocellulose. These are polymers of sugars (pentoses and hexoses). Lignin is a macromolecule which is rich in phenolic motifs. The term "lignocellulosic biomass" means, for example, products obtained from logging operations and by-products obtained from agriculture such as straw, as well as certain high-yield plants such as miscanthus or poplar.

Producing chemical products using lignocellulosic biomass means that the energy dependence on oil can be reduced at the same time as preserving the environment by reducing the emissions of greenhouse gases without using resources intended for food use.

The direct transformation of lignocellulosic biomass or cellulose into products or chemical intermediates, in particular mono- or poly-oxygenated compounds, is a particularly interesting pathway. The term "direct transformation" means the one-step transformation of lignocellulosic biomass or cellulose, optionally pre-treated, into upgradable mono- or poly-oxygenated products.

Upgrading lignocellulosic biomass or cellulose contained in the biomass using a combination of homogeneous and heterogeneous catalysts has been widely described in the literature.

Patent application US2009/0326286 describes the hydrolysis and hydrogenation of lignocellulosic biomasses to monosaccharides in the presence of a homogeneous catalyst and a heterogeneous catalyst. The homogeneous catalyst is described as a mineral or organic Brønsted acid preferably selected from the acids $H_2SO_4$, $H_3PO_4$, $H_3PO_3$, $H_3PO_2$ and $CH_3COOH$. The heterogeneous catalyst is based on activated carbon, silica, zeolites or high molecular weight polymers onto which a transition metal selected from ruthenium, nickel, platinum and palladium has been deposited in quantities in the range 0.1% to 5.5% by weight with respect to the total mass of the heterogeneous catalyst. The products formed and the associated yields are not given.

Sels et al (Chem. Comm. 2010, 46, 3577-3579) studied the transformation of cellulose into hexitols (sorbitol+mannitol) in the presence of a homogeneous catalyst and a heterogeneous catalyst. The homogeneous acid catalysts used were $H_2SO_4$ and $H_4SiW_{12}O_{40}$. The heterogeneous catalyst was Ru/C. The conversion of the microcrystalline cellulose was respectively 50% and 80% with these two acids for a reaction in water at 190° C. and under 50 bars of $H_2$ for 24 h (pH(25° C.)=2). The associated yields of hexitols were 48% and 13%. The ground cellulose had an exacerbated reactivity, with total conversion in 1 h under the same operating conditions and a hexitol yield of 87%.

Albeit with a different aim, Zhang et al (Chem. Comm., 2012, 48, 7052-7054) combined tungstic acid, $H_2WO_4$, which is insoluble in water at ambient temperature, and the heterogeneous catalyst Ru/C to convert cellulose into ethylene glycol in water at 245° C. under 60 bars $H_2$. The particular feature of this system is that tungstic acid dissolves when hot and moves from being heterogeneous to homogeneous during heating to 245° C. The yield of ethylene glycol reached 59%, with complete conversion of the cellulose in 30 min.

More recently, C. Liang (Green Chem., 2013, 15, 891-895) has described a combination of catalysts for the production of ethylene glycol using cellulose, in water at 245° C. under 60 bars $H_2$. The addition of calcium hydroxide $Ca(OH)_2$ in association with the heterogeneous catalyst CuCr meant that the ethylene glycol yield for the reaction could be increased from 5% to 30%. The propylene glycol yield remained stable at about 30-35%.

Finally, in 2009, R. Raines (JACS, 2009, 131, 1979-1985) described the transformation of sugars, cellulose and lignocellulose into 2,5-dimethylfuran in two steps. The first step was carried out in an ionic liquid medium based on DMA-LiCl/[EMIM]Cl at 140° C. for 2 h and was catalysed by a mixture of $CrCl_3$ and HCl, both in a concentration of 10% molar with respect to the cellulose. At the end of this first step, a step for purification by steric exclusion chromatography was carried out and was used to eliminate the chloride ions from the medium in order to prevent poisoning of the catalyst used in the second step. The second step could then be carried out and involved the transformation of the purified solution in the presence of a copper-based catalyst deposited on Ru/C under hydrogen in 1-butanol at 220° C. for 10 h in order to form 2,5-dimethylfuran.

With the exception of these last two examples, respectively pertaining to the use of an alkaline-earth metal salt and the non-simultaneous use in a first step of a homogeneous catalyst comprising a metallic salt and a second homogeneous catalyst based on a Brønsted acid, then in a second step operating under conditions which differ from those of the first using a heterogeneous catalyst, the literature does not describe a process which can allow a direct transformation of cellulose or, more widely, lignocellulosic biomass, which may have been pre-treated, into upgradable mono- or poly-oxygenated products by bringing the lignocellulosic biomass simultaneously into contact, in one and the same reaction medium, with a combination of one or more homogeneous catalysts and one or more heterogeneous catalysts of the type described in the present invention.

Patent application WO2012/035160 from BIOeCON International Holding also described the hydrolysis and hydrogenation of cellobiose and cellulose in an ionic liquid medium as a solvent at temperatures in the range 80° C. to 220° C. in the presence of a heterogeneous catalyst, preferably in the presence of Ru/C. The ionic liquid solvent is preferably a hydrated inorganic salt and in particular $ZnCl_2.4H_2O$ with a cellobiose/$ZnCl_2.4H_2O$ weight ratio of 1/12 and a cellulose/$ZnCl_2.4H_2O$ weight ratio of 1/24. The maximum conversion of cellulose obtained thereby after 6 h was 60%. The sorbitol was formed in a yield of 55%. The transformation was accompanied by the formation of humins. The same research, focussing on cellobiose, has been reported very recently in the following publication: Makkee et al (Catal. Sci. Technol, doi10.1039/c3cy20808g).

The Applicant's research has demonstrated that, surprisingly, bringing lignocellulosic biomass or cellulose into simultaneous contact with a combination of one or more homogeneous catalysts and one or more heterogeneous catalysts in the same reaction chamber operating under specific operating conditions can be used to directly obtain upgradable mono- or poly-oxygenated products and reduce the amount of non-upgradable products such as humins.

SUMMARY OF THE INVENTION

Thus, one aim of the present invention is to provide a process for the transformation of lignocellulosic biomass or cellulose into mono- or poly-oxygenated compounds, in which the lignocellulosic biomass or the cellulose is brought into simultaneous contact with a combination of one or more homogeneous catalysts and one or more heterogeneous catalysts in the same reaction chamber, in the presence of at least one solvent, said solvent being water alone or as a mixture with at least one other solvent, in a reducing atmosphere, and at a temperature in the range 80° C. to 250° C. and at a pressure in the range 0.5 MPa to 20 MPa, said homogeneous catalyst or catalysts comprising a metallic salt which may or may not be hydrated with general formula $MX_n.n'H_2O$ in which M is a metal selected from metals from groups 3 to 16 of the periodic classification, n is a whole number in the range 1 to 6 and n' is a whole number in the range 0 to 6 and X is at least one anion selected from halides, nitrates, carboxylates, halocarboxylates, acetylacetonates, alcoholates, phenolates, which may or may not be substituted, sulphates, alkylsulphates, phosphates, alkylphosphates, halosulphonates, alkylsulphonates, perhaloalkylsulphonates, bis(perhaloalkylsulphonyl) amides, arenesulphonates, which may or may not be substituted with halogen or haloalkyl groups, said anions X possibly being identical or different in the case in which n is greater than 1, said heterogeneous catalyst or catalysts comprising at least one metal selected from metals from groups 6 to 11 and metals from group 14 of the periodic classification and a support selected from oxides of elements selected from aluminium, titanium, silicon, zirconium, cerium and niobium, and mixed oxides selected from zinc, copper and cobalt aluminates, said oxides possibly being doped or not doped with at least one metallic compound selected from tungsten, tin, molybdenum and antimony, used alone or as a mixture, crystalline or non-crystalline aluminosilicates, aluminophosphates and amorphous or crystalline carbon compounds.

In the present invention, reference is made to the new notation for the periodic classification of the elements: Handbook of Chemistry and Physics, 76th edition, 1995-1996.

In the present invention, the term "homogeneous catalyst" means a catalyst which is soluble in the reaction medium.

The term "heterogeneous catalyst" means a catalyst which is not soluble in the reaction medium.

One advantage of the present invention is to allow upgradable mono- or poly-oxygenated products to be obtained directly while limiting the formation of non-upgradable products such as soluble and insoluble humins, i.e. high molecular weight products obtained from unwanted condensations of sugars and their derivatives.

One other advantage of the present invention is that it can be used both to improve the conversion and to improve the conversion kinetics of the lignocellulosic biomass or the cellulose by the simultaneous use, in the same reaction chamber operating under a reducing atmosphere, of the combination of homogeneous and heterogeneous catalysts as claimed.

DETAILED DESCRIPTION OF THE INVENTION

The Feed

The feed treated in the process of the invention is lignocellulosic biomass or cellulose.

Lignocellulosic biomass is essentially constituted by three constituents naturally present in variable quantities depending on its origin: cellulose, hemicellulose and lignin.

Cellulose $(C_6H_{10}O_5)_n$ represents the major portion (40-60%) of the composition of the lignocellulosic biomass. Cellulose is a linear homopolymer composed of many units of D-anhydroglucopyranose (AGU) connected together via $\beta$-(1$\rightarrow$4) glycosidic bonds. The repeat motif is the cellobiose dimer.

Cellulose is insoluble in water at ambient temperature and pressure.

Hemicellulose is the second carbohydrate as regards quantity after cellulose, and constitutes 20% to 40% by weight of the lignocellulosic biomass. In contrast to cellulose, this polymer is primarily constituted by pentose monomers (5-atom cycles) and hexose monomers (6-atom cycles). Hemicellulose is an amorphous heteropolymer with a lower degree of polymerization than that of cellulose (30-100).

Lignin is an amorphous macromolecule present in lignocellulosic compounds in proportions that vary depending on the origin of the material (straw ~15%; wood: 20-26%). Its function is mechanical strength, hydrophobization and support of plants. This macromolecule, which is rich in phenolic motifs, may be described as resulting from the combination of three propyl-methoxy-phenol type monomers. Its molar mass varies from 5000 g/mol to 10000 g/mol for hard woods and reaches 20000 g/mol for soft woods.

Lignocellulosic starting material may advantageously be constituted by wood or vegetable waste. Other non-limiting examples of lignocellulosic biomass material are residues from agricultural exploitation such as straw, grass, stems, kernels or shells, logging waste such as first clearing products, bark, sawdust, chips or shavings, logging products, dedicated cultivation (short rotation coppice), waste from the agroalimentary industry such as waste from the cotton, bamboo, sisal, banana, maize, panicum virgatum, alfalfa, coconut or bagasse, household organic waste, waste from wood transformation facilities and spent construction wood, paper pulp, or paper, recycled or otherwise.

The feed used in the process of the invention is lignocellulosic biomass or cellulose. The cellulose used may be crystalline or amorphous. The feed for the process of the invention may also advantageously comprise cellobiose and amorphous glucose polymers, such as starch or glucose. Finally, the feed may be saccharose.

The lignocellulosic biomass feed may advantageously be used in its unrefined form, i.e. with all of its three constituents, cellulose, hemicellulose and lignin. The unrefined biomass is generally in the form of fibrous residues or powder. It may also advantageously be ground or shredded for transport.

The lignocellulosic biomass feed may advantageously also be used in its pre-treated form, i.e. in a form containing at least one cellulosic portion after extraction of the lignin and/or the hemicellulose.

The biomass preferably undergoes a pre-treatment in order to increase the reactivity and accessibility to the cellulose within the biomass before it is transformed. These pre-treatments are mechanical, thermochemical, thermomechanical and chemical and/or biochemical in nature and cause de-crystallization of the cellulose, a reduction in the degree of polymerization of the cellulose, dissolution of the hemicellulose and/or lignin and/or cellulose or partial hydrolysis of the hemicellulose and/or the cellulose following the treatment.

The lignocellulosic biomass feed may also be pre-treated in order to be in the form of hydrosoluble oligomers. These pre-treatments are mechanical, thermochemical, thermomechanical and chemical and/or biochemical in nature. They cause de-crystallization and dissolution of all or a portion of the cellulose in the form of hydrosoluble oligomers.

The mechanical treatments go beyond simple shredded as they modify the chemical structure of the constituents. They improve accessibility to and reactivity of the cellulose by its de-crystallization and by increasing the surface area for exchange. The mechanical treatments include reduction of the size of the fibres or elementary particles, for example by chipping the biomass using a cutter, by grinding the biomass (adjusting the granulometry), deconstructing the chips on a press or defibration by abrasion of the chips, after preheating. The mechanical treatments may be operated in a decentralized mode close to the production of biomass, or in a centralized mode feeding directly into the transformation.

The thermochemical treatments including digesting the biomass at high temperature (150-170° C.) in a dilute acid medium (principally sulphuric acid, but also phosphoric acid, acetic acid or formic acid), in an alkaline medium (sodium hydroxide, sulphites, lime, etc.), in an oxidizing medium (moist oxidation in air or in oxygen; peroxide in alkaline medium; peracetic acid) and in unconventional media such as ionic liquids (for example 1-ethyl-3-methyl-imidazolium acetate [emim][OAc]) or hydrated inorganic salts ($FeCl_3 \cdot 6H_2O$, $ZnCl_2 \cdot 5H_2O$) used as solvents. The other thermochemical treatments include treatments with solvents (hot ethanol) or torrefaction, which can be defined as a pyrolysis at a moderate temperature with a controlled residence time as it is accompanied by a partial destruction of the lignocellulosic material. Examples of known torrefaction technologies are rotary furnace, moving bed, fluidized bed, heated endless screw, and contact with metallic beads supplying heat. These technologies may optionally use a gas moving as a co- or counter-current, such as nitrogen or any other gas which is inert under the reaction conditions.

The thermomechanical-chemical treatments include steam treatments (steam explosion, also known as flash hydrolysis), AFEX (ammonia fibre explosion) treatment or twin screw extrusion with various chemical reagents.

The pre-treatment can be used to prepare the lignocellulosic biomass by separating the carbohydrate portion from the lignin and adjusting the size of the particles of biomass to be treated. The size of the biomass particles after pre-treatment is generally less than 5 mm, preferably less than 500 microns.

The Catalysts

In accordance with the invention, the lignocellulosic biomass or cellulose is brought into contact in the process of the invention simultaneously with a combination of one or more homogeneous catalysts and one or more heterogeneous catalysts in the same reaction chamber, in the presence of at least one solvent, said solvent being water alone or as a mixture with at least one other solvent, in a reducing atmosphere, and at a temperature in the range 80° C. to 250° C. and at a pressure in the range 0.5 MPa to 20 MPa.

An essential criterion of the present invention resides in bringing said feed into contact under operating conditions as claimed, simultaneously with a combination of one or more homogeneous catalysts and one or more heterogeneous catalysts within the same reaction chamber.

In fact, the reactions occurring in the process for the transformation of the lignocellulosic biomass or cellulose are not successive reactions because of the simultaneous use and operation of a combination of one or more homogeneous catalysts and one or more heterogeneous catalysts in the same reaction chamber.

Cellulose dissolution induced by the homogeneous catalyst or catalysts and the transformation of the dissolved products by the heterogeneous catalyst or catalysts is thus carried out in a concomitant and complementary manner. Thus, it is possible to exploit this compatibility between the homogeneous and heterogeneous catalysts to advantage in order to dispense with any intermediate treatment or purification work, which is synonymous with supplemental process costs and large losses of material associated with this step.

Preferably, said process of the invention is not operated in two successive steps.

Preferably, the lignocellulosic biomass or the cellulose is brought into simultaneous contact with a combination of one or more homogeneous catalysts and with a heterogeneous catalyst in the same reaction chamber.

More preferably, the lignocellulosic biomass or the cellulose is brought into simultaneous contact in the same reaction chamber with a combination of a homogeneous catalyst and a heterogeneous catalyst.

In accordance with the invention, said homogeneous catalyst or catalysts comprise a metallic salt which may or may not be hydrated with general formula $MX_n \cdot n'H_2O$ in which M is a metal selected from the metals from groups 3 to 16 of the periodic classification, n is a whole number in the range 1 to 6 and n' is a whole number in the range 0 to 6 and X is at least one anion selected from halides, nitrates, carboxylates, halocarboxylates, acetylacetonates, alcoholates, phenolates, which may or may not be substituted, sulphates, alkylsulphates, phosphates, alkylphosphates, halosulphonates, alkylsulphonates, perhaloalkylsulphonates, bis(perhaloalkylsulphonyl)amides, arenesulphonates, which may or may not be substituted with halogen or haloalkyl groups, said anions X possibly being identical or different in the case in which n is greater than 1.

Said metal M selected from groups 3 to 16 of the periodic classification in the homogeneous catalyst of the invention is preferably selected from the following metals: Al, Sc, Ti, V, Cr, Mn, Fe, Co, Ni, Cu, Zn, Ga, Ge, Y, Zr, Nb, Mo, Tc, Ru, Rh, Pd, Ag, Cd, In, Sn, Sb, La, Hf, Ta, W, Re, Os, Ir, Pt, Au, Hg, Tl, Pb, Bi, Po, Ac, Rf, Db, Sg, Bh, Hs, Mt, Ds, Rg, Uub.

Preferably, said metal M is selected from the following metals: Al, Sc, Ti, Cr, Mn, Fe, Co, Ni, Cu, Zn, Al, Ga, Y, Zr, Mo, In, Sn, La, Hf, Ta, W, Pb, Bi.

Highly preferably, said metal M is selected from the following metals: Cr, Mn, Fe, Co, Ni, Cu, Zn, Al, Ga, In, Cu, Zr, Bi, La and Sn. More preferably, said metal M is selected from the metals: Cr, Mn, Fe, Zn, Al, Sn, Cu, Zr, Bi and La.

Still more preferably, said metal M is selected from the metals: Fe, Zn, Al, Sn, Cu and La.

In accordance with the invention, in the composition of the metallic salt, the metal M selected from the cited metals is associated with one or more anions X which may be identical or different.

Preferably, the anion X is at least one anion selected from halides, alkylsulphonates, perhaloalkylsulphonates and bis(perhaloalkylsulphonyl)amides.

Preferably, the halide is the fluoride, the chloride, the bromide or the iodide.

Preferably, the alkylsulphonate is the mesylate and the tosylate.

Preferably, the perhaloalkylsulphonate is the triflate.

Preferably, the bis(perhaloalkylsulphonyl)amide is the bis(triflimide).

Highly preferably, in the case in which n equals 3, the anion X is a chloride.

Preferred said homogeneous catalyst or catalysts comprise a metallic salt, which may or may not be hydrated, with general formula $MX_a.n'H_2O$, n and n' having the meanings given above, in which M is a metal selected from the metals Cr, Mn, Fe, Co, Ni, Cu, Zn, Al, Ga, In, and Sn and X is at least one anion selected from halides, alkylsulphonates, perhaloalkylsulphonates, bis(perhaloalkylsulphonyl)amides, said anions X possibly being identical or different in the case in which n is greater than 1.

More preferred said homogeneous catalyst or catalysts comprise a metallic salt which may or may not be hydrated with general formula $MX_n.n'H_2O$, n and n' having the meanings given above, in which M is a metal selected from the metals Cr, Fe, Zn, Al and Sn, and X is at least one anion selected from the fluoride, the chloride, the bromide, the iodide, the mesylate, the tosylate, the triflate and the bis(triflimide), said anions X possibly being identical or different in the case in which n is greater than 1.

In the case in which a plurality of homogeneous catalysts are used, said homogeneous catalyst(s) are advantageously selected from metallic salts which may or may not be hydrated with general formula $MX_n.n'H_2O$, n and n' having the meanings given above, in which M is a metal selected from the metals Cr, Fe, Zn, Al and Sn, and X is at least one anion selected from the fluoride, the chloride, the bromide, the iodide, the mesylate, the tosylate, the triflate and the bis(triflimide), said anions X possibly being identical or different in the case in which n is greater than 1 and said homogeneous catalysts possibly being identical or different.

In accordance with the invention, said heterogeneous catalyst or catalysts comprise at least one metal selected from metals from groups 6 to 11 and metals from group 14 of the periodic classification and a support selected from oxides of elements selected from aluminium, titanium, silicon, zirconium, cerium and niobium, and mixed oxides selected from zinc, copper and cobalt aluminates, said oxides possibly being doped or not doped with at least one metallic compound selected from tungsten, tin, molybdenum and antimony, used alone or as a mixture, crystalline or non-crystalline aluminosilicates, aluminophosphates and amorphous or crystalline carbon compounds.

Said metal selected from metals from groups 6 to 11 and the metals from group 14 of the periodic classification in the heterogeneous catalyst or catalysts of the invention are preferably selected from the following metals: Cr, Mo, W, Mn, Tc, Re, Fe, Ru, Os, Co, Rh, Ir, Ni, Pd, Pt, Cu, Ag, Au, Zn, Cd, and Hg, on the one hand, and from: Ge, Sn and Pb on the other hand, alone or as a mixture.

Preferably, said metal is selected from the metals Mo, W, Re, Ru, Co, Rh, Ir, Ni, Pd, Pt, Cu, on the one hand and Sn on the other hand, alone or as a mixture.

In accordance with a preferred embodiment, the following mixtures of metals are preferred: NiSn, RePt, FePt, SnPt, CuPt, IrPt, CoPt, RhPt, OsPt, RuRe, PdRe, RuSn and RuPt.

In accordance with a highly preferred embodiment, said metal is platinum.

Preferably, the quantity of metal on said heterogeneous catalyst or catalysts is advantageously in the range 0.01% to 10% by weight, preferably in the range 0.1% to 5% by weight with respect to the total mass of said heterogeneous catalyst or catalysts.

The metal or metals of the heterogeneous catalysts of the invention are advantageously deposited on a support.

In accordance with the invention, said heterogeneous catalyst or catalysts comprise a support selected from oxides of elements selected from alumina, titanium, silica, zirconia, cerium, niobium, and mixed oxides selected from zinc, copper and cobalt aluminates, said oxides possibly being doped or not doped with at least one metallic compound selected from tungsten, tin, molybdenum and antimony, used alone or as a mixture, crystalline or non-crystalline aluminosilicates, aluminophosphates and amorphous or crystalline carbon compounds.

Preferably, the crystalline or non-crystalline aluminosilicates are selected from zeolites and mesostructured solids.

Preferably, the amorphous or crystalline carbon compounds are selected from activated carbon, carbon black, carbon nanotubes, mesostructured carbon and carbon fibres.

In the case in which said support is selected from oxides of elements selected from doped aluminium, titanium, silicon, zirconium, cerium and niobium, a metallic element preferably selected from tungsten, tin, antimony and molybdenum is advantageously added to said support, alone or as a mixture. Preferably, the quantity of the metallic element selected from tungsten, tin, antimony and molybdenum, alone or as a mixture, is advantageously in the range 0.1% to 30% by weight, preferably in the range 1% to 20% by weight with respect to the total mass of said catalyst.

Said support is preferably hydrothermally stable, i.e. stable under conditions combining water and temperature. Thus, the support may undergo a treatment step aimed at improving its stability under the hydrothermal conditions of the reaction. As an example, the surface may be passivated, a carbon film may be deposited, or an oxide may be deposited.

The metal or metals selected from groups 6 to 11 and the metals from group 14 of the periodic classification may generally be deposited on said support for the heterogeneous catalyst or catalysts of the invention by using a precursor of the metal or metals. As an example, it may be an organometallic complex, a salt of metals such as metallic chlorides, or metallic nitrates.

The metal or metals may advantageously be introduced using any technique which is known to the skilled person, such as ion exchange dry impregnation, excess impregnation, vapour phase deposition, etc., for example. The metal may be introduced before or after shaping the support.

The step for introducing the metal or metals may advantageously be followed by a heat treatment step. The heat treatment is advantageously carried out between 300° C. and 700° C. in an atmosphere of oxygen or air. The heat treatment step may be followed by a temperature reduction step. The heat treatment reduction is advantageously carried out at a temperature in the range 200° C. to 600° C. in a stream or atmosphere of hydrogen.

Preferably, said heterogeneous catalyst or catalysts also undergo a reduction step in situ, i.e. in the reactor in which the reaction takes place, before introducing the reactional feed. Said reduction step may also advantageously be carried out ex situ.

The size of the metallic particles of the heterogeneous catalyst or catalysts employed in the process of the invention is preferably less than 10 nm.

The heterogeneous catalyst or catalysts used in the present invention may be in the form of a powder, extrudates, beads or pellets. Shaping may be carried out before or after introducing the metal.

The heterogeneous catalyst or catalysts used in the present invention are characterized by techniques which are known to the skilled person. An example which may be cited to characterize the metallic phase is transmission microscopy.

Transformation Process

In accordance with the invention, the process for the transformation of the lignocellulosic biomass or cellulose is carried out in a reaction chamber in the presence of at least one solvent, said solvent being water alone or as a mixture with at least one other solvent, in a reducing atmosphere, and at a temperature in the range 80° C. to 250° C., and at a pressure in the range 0.5 MPa to 20 MPa.

Thus, the process is carried out in a reaction chamber comprising at least one solvent and in which the feed is brought into the presence of the catalytic system of the invention.

In accordance with the invention, the process of the invention is operated in the presence of at least one solvent, said solvent being water alone or as a mixture with at least one other solvent.

In accordance with a preferred embodiment, the process of the invention is operated in the presence of water mixed with at least one alcohol or at least one organic solvent, under sub- or super-critical conditions.

The alcohols are advantageously selected from methanol, ethanol and the propanols.

The organic solvents may advantageously be selected from tetrahydrofuran and ethyl acetate.

In the case in which said process of the invention is operated in the presence of water mixed with at least one other solvent, the mixture of solvents comprises a quantity by weight of water of more than 5% by weight and preferably more than 30%, and highly preferably more than 50% with respect to the total mass of said mixture.

In accordance with another embodiment, the process of the invention is operated in the presence of water alone.

Preferably, the process of the invention is operated in the presence of at least one solvent with the exception of solvents selected from ionic liquids.

In accordance with the invention, the process for the transformation of lignocellulosic biomass or cellulose of the invention is carried out in a reducing atmosphere, preferably in an atmosphere of hydrogen. The hydrogen may be used pure or as a mixture.

Preferably, said process of the invention is operated at a temperature in the range 150° C. to 240° C., and at a pressure in the range 2 MPa to 10 MPa.

In general, the process may be operated in accordance with various implementational embodiments. Thus, the process may advantageously be carried out continuously or in batches, for example in a fixed bed. A closed or semi-open reaction chamber may be used for the operation.

The homogeneous catalyst or catalysts are advantageously introduced into the reaction chamber in a quantity corresponding to a biomass/homogeneous catalyst(s) ratio by weight in the range 1 to 1000, preferably in the range 10 to 500.

The heterogeneous catalyst or catalysts are introduced into the reaction chamber in a quantity corresponding to a biomass/heterogeneous catalyst(s) ratio by weight in the range 1 to 1000, preferably 1 to 500, preferably in the range 1 to 100, preferably in the range 1 to 50 and more preferably in the range 1 to 25.

The heterogeneous catalyst or catalysts introduced into the reactor may undergo a reducing heat treatment step before introducing the reaction feed. The reducing heat treatment is preferably carried out at a temperature in the range 150° C. to 600° C. in a stream or atmosphere of hydrogen.

The biomass is introduced into the process in a quantity corresponding to a solvent/biomass ratio by weight in the range 10 to 1000, preferably in the range 1 to 500 and more preferably in the range 5 to 100.

Considering a continuous process, the hourly space velocity (flow rate of feed by weight/mass of heterogeneous catalyst(s)) is in the range 0.01 to 5 $h^{-1}$, preferably in the range 0.02 to $2^{-1}$.

The Products Obtained and Their Mode of Analysis

The reaction products for the transformation process of the invention are mono- or poly-oxygenated compounds. Said mono- or poly-oxygenated compounds are soluble in water.

Said mono- or poly-oxygenated compounds are advantageously constituted by monosaccharides and their derivatives, oligosaccharides, and also soluble polymers advantageously formed by successive combinations of monosaccharide derivatives.

The term "monosaccharides" means a carbohydrate with composition $C_nH_{2n}O_n$ where n is more than 2, obtained by complete hydrolysis of cellulose, or hemicellulose, or starch. Monosaccharides are simple sugars which are produced by complete depolymerisation of cellulose and/or hemicellulose such as in particular, glucose, mannose, xylose, fructose etc.

The term "monosaccharide derivatives" denotes products which may be obtained by dehydration, isomerization, reduction or oxidation:
  alcohol sugars, alcohols and polyols: in particular sorbitol, anhydrosorbitol, hexanetetrols, hexanetriols, hexanediols, xylitol, pentanetetrols, pentanetriols, pentanediols, erythritol, butanetriols, butanediols, glycerol, 1,3-propanediol, propylene glycol, ethylene glycol, hexanols, pentanols, butanols, propanols, ethanol etc.;
  ketones, hexane-diones: 2,5-hexanedione, hydroxyacetone etc.;
  carboxylic acids and their esters, lactones: formic acid, alkyl formates, acetic acid, alkyl acetates, hexanoic acid, alkyl hexanoates, levulinic acid, alkyl levulinates, lactic acid, alkyl lactates, glutaric acid, alkyl glutarates, 3-hydroxypropanoic acid, 3-hydroxybutyrolactone, γ-butyrolactone, γ-valerolactone;
  cyclic ethers: examples are tetrahydrofuran (THF), 3-methyltetrahydrofuran (Me-THF) and its positional isomers, 2,4-dimethyltetrahydrofuran and its positional isomers, tetrahydropyran-2-methanol and its positional isomers;

furans: furan-2,5-dicarboxylic acid, 5-(hydroxymethyl) furfural, furfural etc.

The term "soluble polymers" denotes all products obtained from condensation between monosaccharides, oligosaccharides and/or monosaccharide derivatives.

At the end of the reaction, the reaction medium is removed and centrifuged. The reaction liquid is then analysed by high pressure liquid chromatography (HPLC) and by gas chromatography (GC) using refractometry in order to determine the quantity of conversion products in the aqueous solution.

The quantity of water-soluble reaction products (monosaccharides and derivatives, oligosaccharides, soluble polymers) is determined by TOC (Total Organic Carbon) analysis, which consists of measuring dissolved carbon. The quantity of monosaccharides and their derivatives is determined by HPLC analyses.

EXAMPLES

In the examples below, the tungstated zirconia catalyst ($ZrO_2$—$WO_x$) was commercially available and provided by the firm MEL Chemicals and contained 10.3% by weight of tungsten.

The iron chloride hexahydrate was commercially available and used without purification.

Example 1: Preparation of Catalyst C1: 0.5% by Weight Pt/$ZrO_2$—$WO_x$

An aqueous solution of hexachloroplatinic acid $H_2PtCl_6.xH_2O$, 1.9% by weight (25 mL, 0.475 g) was added at ambient temperature to the $ZrO_2$—$WO_x$ support (24 g) which had been desorbed under vacuum (1 h, 100° C.). The mixture was stirred for one hour and was then evaporated off. The solid obtained was then placed in an oven to dry at 110° C. for 24 h. Next, the solid was calcined in a flow of dry nitrogen at a temperature of 150° C. for 1 h, then 250° C. for 1 h, then 350° C. for 3 h and finally 420° C. for 4 h. It was then reduced in a stream of hydrogen at 500° C. for two hours. Catalyst C1 obtained contained 0.5% by weight of platinum.

Example 2: Transformation of Cellulose Without Catalyst

This example concerns the conversion of cellulose without catalyst for the production of mono- and poly-oxygenated products.

50 mL of water and 1.3 g of SigmaCell® cellulose were introduced into a 100 mL autoclave. The autoclave was heated to 190° C. and a pressure of 5 MPa of nitrogen was introduced. After 24 h of reaction, the reaction medium was removed and centrifuged. The reaction liquid was then analysed by high pressure liquid chromatography (HPLC) using refractometry in order to determine the quantity of conversion products in the aqueous solution.

The results obtained are shown in Table 1.

Example 3: Transformation of Cellulose Using $ZrO_2$—$WO_x$

This example concerns the conversion of cellulose using commercial tungstated zirconia for the production of mono- and poly-oxygenated products.

50 mL of water, 1.3 g of SigmaCell® cellulose and 0.55 g of tungstated zirconia were introduced into a 100 mL autoclave. The autoclave was heated to 190° C. and a pressure of 5 MPa of nitrogen was introduced. After 24 h of reaction, the reaction medium was removed and centrifuged. The reaction liquid was then analysed by high pressure liquid chromatography (HPLC) using refractometry in order to determine the quantity of conversion products in the aqueous solution.

The results obtained are shown in Table 1.

Example 4: Transformation of Cellulose Using Iron Chloride Hexahydrate Alone

This example concerns the conversion of cellulose using iron chloride hexahydrate for the production of mono- and poly-oxygenated products.

50 mL of water, 1.3 g of SigmaCell® cellulose and 0.03 g of iron chloride hexahydrate were introduced into a 100 mL autoclave. The autoclave was heated to 190° C. and a pressure of 5 MPa of nitrogen was introduced. After 24 h of reaction, the reaction medium was removed and centrifuged. The reaction liquid was then analysed by high pressure liquid chromatography (HPLC) using refractometry in order to determine the quantity of conversion products in the aqueous solution.

The results obtained are shown in Table 1.

Example 5: Transformation of Cellulose Using the Catalyst C1 (0.5% by Weight. Pt/$ZrO_2$—$WO_x$)

This example concerns the conversion of cellulose using catalyst C1 described in Example 1 for the production of mono- and poly-oxygenated products.

50 mL of water, 1.3 g of SigmaCell® cellulose and 0.55 g of catalyst C1 were introduced into a 100 mL autoclave under an atmosphere of nitrogen. The autoclave was heated to 190° C. and a pressure of 5 MPa of nitrogen was introduced. After 24 h of reaction, the reaction medium was removed and centrifuged. The reaction liquid was then analysed by high pressure liquid chromatography (HPLC) and gas chromatography (GC) using refractometry in order to determine the quantity of conversion products in the aqueous solution.

The results obtained are shown in Table 1.

Example 6: Transformation of Cellulose Using Catalyst C1 (0.5% by Weight of Pt/$ZrO_2$—$WO_x$) in Combination with Iron Chloride Hexahydrate $FeCl_3.6H_2O$ (in Accordance with the Invention)

This example concerns the conversion of cellulose using a combination of catalyst C1 described in Example 1 and iron chloride hexahydrate for the production of mono- and poly-oxygenated products.

50 mL of water, 1.3 g of SigmaCell® cellulose, 0.03 g of iron chloride hexahydrate and 0.55 g of catalyst C1 were introduced into a 100 mL autoclave under an atmosphere of nitrogen. The autoclave was heated to 190° C. and a pressure of 5 MPa of nitrogen was introduced. After 24 h of reaction, the reaction medium was removed and centrifuged. The reaction liquid was then analysed by high pressure liquid chromatography (HPLC) using refractometry in order to determine the quantity of conversion products in the aqueous solution.

The results obtained are shown in Table 1.

Dissolution is defined as the percentage dissolution of biomass or cellulose in solution and is calculated using the following equation:

$$\text{Dissolution}(\%) = 100 * C_{dissolved} / C_{initial}$$

in which $C_{dissolved}$ represents the quantity of dissolved carbon analysed by TOC (mg) and $C_{initial}$ represents the quantity of carbon at the start of the reaction contained in the biomass or solid cellulose.

The product yields were calculated using HPLC analysis. The yields indicated for a derivative i were calculated as follows:

$$\text{Yield }(i) = \frac{C(i)(g/l)}{Cdissolved(g(C)/l)} \times \frac{n \times M(C)(g/\text{mol})}{M(i)(g/\text{mol})}$$

where C(i) represents the concentration of the derivative i determined by HPLC, n represents the number of carbon atoms in the derivative i, M(C) represents the molar mass of the carbon atom, and M(i) represents the molar mass of the derivative.

TABLE 1

Dissolution of cellulose and formation of humins

| Examples | Catalyst | Dissolution at 6 h | Dissolution at 12 h | Dissolution at 24 h | Formation of humins |
|---|---|---|---|---|---|
| 2 | No catalyst | 18% | 22% | 25% | + |
| 3 | ZrW | 35% | 42% | 50% | + |
| 4 | FeCl₃ | 50% | 52% | 50% | ++ |
| 5 | Pt/ZrW (C1) | 37% | 50% | 60% | No humins |
| 6 | FeCl₃ + PtZrW (C1) | 80% | 90% | 92% | No humins |

By way of example, the carbon into mono- and poly-oxygenated product yields obtained by the transformation of cellulose in the presence of a combination of $FeCl_3$ and PtZrW were as follows: propylene glycol (14%), ethylene glycol (8%), 1,2,6-hexanetriol (8%), 1,2-hexanediol (8%), 2,4-dimethyltetrahydrofuran (8%), 1,2-butanediol (5%), erythritol (3%), glycerol (2%), 3-methyltetrahydrofuran (3%), ethanol (2%), propanol (2%), 2-methylpentanol (2%), glucose (1%), lactic acid (1%), 1,2-pentanediol (1%), 1-pentanol (1%), tetrahydropyrane-2-methanol (1%), methanol (1%).

Example 7: Transformation of Cellulose Using Catalyst C1 (0.5% by Weight $Pt/ZrO_2$—$WO_x$) in Combination with a Homogeneous Catalyst (in Accordance with the Invention)

This example concerns the conversion of cellulose using a combination of catalyst C1 described in Example 1 and a metallic salt for the production of mono- and poly-oxygenated products.

50 mL of water, 1.3 g of SigmaCell® cellulose, a metallic salt and 0.55 g of catalyst C1 were introduced into a 100 mL autoclave under an atmosphere of nitrogen. The metallic salts were soluble in water (T=25° C., P=atmospheric pressure). The mass of the added metallic salt is described in Table 2.

The autoclave was heated to 190° C. and a pressure of 5 MPa of nitrogen was introduced. After 24 h of reaction, the reaction medium was removed and centrifuged. Samples were also taken during the tests and analysed by high pressure liquid chromatography (HPLC) using refractometry in order to determine the quantity of conversion products in the aqueous solution.

The results obtained are shown in Table 2.

TABLE 2

Dissolution of cellulose and formation of humins

| Catalyst | Mass of metallic salt (g) | Dissolution at 6 h (%) | Dissolution at 12 h (%) | Formation of humins |
|---|---|---|---|---|
| FeCl₃ + PtZrW (C1) | 0.033 | 80 | 90 | No humins |
| CrCl₃ + PtZrW (C1) | 0.034 | 81 | 84 | No humins |
| ZnCl₂ + PtZrW (C1) | 0.007 | 39 | 54 | No humins |
| CuCl₂ + PtZrW (C1) | 0.011 | 44 | 66 | No humins |
| MnCl₂ + PtZrW (C1) | 0.017 | 34 | 49 | No humins |
| AlCl₃ + PtZrW (C1) | 0.054 | 91 | 96 | No humins |
| SnCl₄ + PtZrW (C1) | 0.026 | 46 | 91 | No humins |
| BiCl₃ + PtZrW (C1) | 0.012 | 26 | 23 | No humins |
| LaCl₃ + PtZrW (C1) | 0.025 | 32 | 91 | No humins |
| ZrCl₄ + PtZrW (C1) | 0.015 | 47 | 69 | No humins |

Example 8: Transformation of a Lignocellulosic Biomass Based on Miscanthus Using Tungstated Zirconia $ZrO_2$—$WO_x$ Alone This example concerns the conversion of a lignocellulosic biomass based on miscanthus using commercial tungstated zirconia for the production of mono- and poly-oxygenated products.

50 mL of water, 5.9 g of lignocellulosic biomass based on miscanthus (equivalent to 1.3 g of cellulose) and 0.55 g of tungstated zirconia were introduced into a 100 mL autoclave. The autoclave was heated to 190° C. and a pressure of 5 MPa of nitrogen was introduced. After 24 h of reaction, the reaction medium was removed and centrifuged. The reaction liquid was then analysed by high pressure liquid chromatography (HPLC) using refractometry in order to determine the quantity of conversion products in the aqueous solution.

The results obtained are shown in Table 3.

Example 9: Transformation of a Lignocellulosic Biomass Based on Miscanthus Using Iron Chloride Hexahydrate Alone This example concerns the conversion of a lignocellulosic biomass based on miscanthus using iron chloride hexahydrate for the production of mono- and poly-oxygenated products.

50 mL of water, 5.9 g of lignocellulosic biomass based on miscanthus (equivalent to 1.3 g of cellulose) and 0.03 g of iron chloride hexahydrate were introduced into a 100 mL autoclave. The autoclave was heated to 190° C. and a pressure of 5 MPa of nitrogen was introduced. After 24 h of reaction, the reaction medium was removed and centrifuged. The reaction liquid was then analysed by high pressure liquid chromatography (HPLC) using refractometry in order to determine the quantity of conversion products in the aqueous solution.

The results obtained are shown in Table 3.

Example 10: Transformation of a Lignocellulosic Biomass Based on Miscanthus Using Catalyst C1 in Combination with Iron Chloride Hexahydrate (in Accordance with the Invention)

This example concerns the conversion of cellulose using a combination of catalyst C1 described in Example 1 and iron chloride hexahydrate for the production of mono- and poly-oxygenated products.

50 mL of water, 5.9 g of lignocellulosic biomass based on miscanthus (equivalent to 1.3 g of cellulose), 0.03 g of iron chloride hexahydrate and 0.55 g of catalyst C1 were introduced into a 100 mL autoclave. The autoclave was heated to 190° C. and a pressure of 5 MPa of nitrogen was introduced. After 24 h of reaction, the reaction medium was removed and centrifuged. The reaction liquid was then analysed by high pressure liquid chromatography (HPLC) and gas chromatography (GC) using refractometry in order to determine the quantity of conversion products in the aqueous solution.

The results obtained are shown in Table 3.

TABLE 3

Dissolution of lignocellulosic biomass based on miscanthus

| Examples | Catalyst | Dissolution at 6 h and 12 h | Dissolution at 24 h | Formation of humins |
|---|---|---|---|---|
| 8 | ZrW | 28% and 30% | 35% | + |
| 9 | $FeCl_3$ | 66% and 65% | 58% | ++ |
| 10 | $FeCl_3$ + PtZrW (C1) | 95% and 96% | 98% | No humins |

By way of example, the carbon yields in mono- or poly-oxygenated products obtained by transformation of lignocellulosic biomass based on miscanthus in the presence of a combination of $FeCl_3$ and PtZrW were as follows: propylene glycol (16%), 1,2-hexanediol (16%), ethylene glycol (9%), 1,2-butanediol (6%), 2,4-dimethyltetrahydrofuran (6%), acetic acid (4%), lactic acid (3%), 1,2,6-hexanetriol (3%), erythritol (3%), glycerol (2%), 3-methyltetrahydrofuran (2%), ethanol (1%), propanol (1%), 2-methylpentanol (1%), glucose (1%), 1,2-pentanediol (1%), 1-pentanol (1%), tetrahydropyrane-2-methanol (1%), methanol (1%).

The association of a homogeneous catalyst (iron chloride hexahydrate) and a heterogeneous catalyst (PtZrW) was shown to be more effective compared with the homogeneous catalyst alone and the heterogeneous catalyst alone.

A maximum conversion improved by 53% was observed using the combination of catalyst C1 described in Example 1 and iron chloride hexahydrate compared with catalyst C1 described in Example 1 used alone, and a conversion improved by 84% compared with iron chloride hexahydrate used alone.

Accelerated dissolution kinetics were observed using the combination of catalyst C1 described in Example 1 and iron chloride hexahydrate compared with catalyst C1 described in Example 1 used alone and compared with iron chloride hexahydrate used alone.

Complete disappearance of the formation of humins was observed using the combination of catalyst C1 described in Example 1 and iron chloride hexahydrate compared with iron chloride hexahydrate used alone.

Example 11: Preparation of Catalyst C2: 2.1% by Weight $Pt/ZrO_2$—$WO_x$

An aqueous solution of hexachloroplatinic acid $H_2PtCl_6$ (22 mL, 1.05 g of Pt) was added at ambient temperature to $ZrO_2$—$WO_x$ support (50 g) which had already been desorbed under vacuum (1 h, 100° C.). The mixture was stirred for one hour, then the solid obtained was oven dried at 120° C. for 24 h. Next, the solid was calcined at a temperature of 150° C. for 1 h, then 250° C. for 1 h, then 350° C. for 3 h and finally 420° C. for 4 h. It was then reduced in a flow of hydrogen at 500° C. for two hours. Catalyst C2 obtained contained 2.1% by weight of platinum.

Example 12: Preparation of Heterogeneous Catalysts Containing Platinum

A series of catalysts was prepared by impregnating simple or mixed oxide supports or carbon-containing supports with a solution of hexachloroplatinic acid. The target Pt metal content was 0.5% with respect to the weight of catalyst.

After impregnation, the prepared catalysts were dried for 24 h at 120° C., then calcined in a flow of air at a temperature of 150° C. for 1 h, then 250° C. for 1 h, then 350° C. for 3 h and finally 420° C. for 4 h. The catalysts were then reduced in a flow of hydrogen at 500° C. for two hours.

The prepared catalysts are described in Table 4.

TABLE 4

Heterogeneous catalysts containing platinum

| Catalyst | Support | Pt content (% by weight) |
|---|---|---|
| C2 | $ZrO_2$—$WO_x$ | 2.1 |
| C3 | $ZrO_2$ | 0.5 |
| C4 | $SiO_2$—$Al_2O_3$ | 0.5 |
| C5 | $CeO_2$—$ZrO_2$ | 0.5 |
| C6 | $TiO_2$—$WO_x$ | 0.5 |
| C7 | C | 0.5 |
| C8 | $ZnAl_2O_4$ | 0.5 |
| C9 | $ZrO_2$—MoOx | 0.5 |

Example 13: Transformation of Cellulose Using Catalysts C3, C4, C5, C6, C7, C8, C9 in Combination with Iron Chloride Hexahydrate (in Accordance with the Invention)

This example concerns the conversion of cellulose using a combination of a catalyst C3, C4, C5, C6, C7, C8, C9 described in Example 8 and a metallic salt for the production of mono- and poly-oxygenated products.

50 mL of water, 1.3 g of SigmaCell® cellulose, 0.03 g of iron chloride and 0.55 g of catalyst were introduced into a 100 mL autoclave. The iron chloride hexahydrate was soluble in water (T=25° C., P=atmospheric P).

The autoclave was heated to 190° C. and a pressure of 5 MPa of nitrogen was introduced. After 12 h of reaction, the reaction medium was removed and centrifuged. Samples were also taken during the tests and analysed by high pressure liquid chromatography (HPLC) using refractometry in order to determine the quantity of conversion products in the aqueous solution.

The results obtained are shown in Table 5.

TABLE 5

Dissolution of cellulose and formation of humins

| Catalysts | Name of catalyst | Dissolution at 6 h (%) | Dissolution at 12 h (%) | Formation of humins |
|---|---|---|---|---|
| $FeCl_3$ + $Pt/ZrO_2$—WOx | $FeCl_3$ + C2 | 72 | 85 | No humins |
| $FeCl_3$ + $Pt/ZrO_2$ | $FeCl_3$ + C3 | 73 | 84 | No humins |
| $FeCl_3$ + $Pt/SiO_2$—$Al_2O_3$ | $FeCl_3$ + C4 | 69 | 84 | No humins |
| $FeCl_3$ + $Pt/CeO_2$—$ZrO_2$ | $FeCl_3$ + C5 | 58 | 79 | No humins |

TABLE 5-continued

Dissolution of cellulose and formation of humins

| Catalysts | Name of catalyst | Dissolution at 6 h (%) | Dissolution at 12 h (%) | Formation of humins |
|---|---|---|---|---|
| FeCl$_3$ + Pt/TiO$_2$—WOx | FeCl$_3$ + C6 | 51 | 53 | No humins |
| FeCl$_3$ + Pt/C | FeCl$_3$ + C7 | 65 | 78 | No humins |
| FeCl$_3$ + Pt/ZnAl$_2$O$_4$ | FeCl$_3$ + C8 | 50 | 54 | No humins |
| FeCl$_3$ + Pt/ZrO$_2$—MoOx | FeCl$_3$ + C9 | 65 | 72 | No humins |

Example 14: Preparation of Heterogeneous Catalysts Containing Zirconium Oxide A series of catalysts was prepared by impregnating a zirconium oxide support (ZrO$_2$, monoclinic) with a solution containing a noble metal.

Catalyst C10 was prepared by impregnating a zirconium oxide support (MEL Chemicals) with a solution of H$_2$PtCl$_6$. After impregnation, the solid was dried for 24 h at 120° C. then calcined in a flow of air at a temperature of 500° C. for 4 h. The solid was reduced in a stream of hydrogen at 500° C. for two hours. Catalyst C10 contained 1.2% by weight of platinum.

Catalyst C11 was prepared by impregnating a zirconium oxide support (MEL Chemicals) with a solution of H$_2$PdCl$_6$. After impregnation, the solid was dried for 24 h at 120° C. then calcined in a flow of air at a temperature of 450° C. for 4 h. The solid was reduced in a stream of hydrogen at 250° C. for two hours. Catalyst C11 contained 1.1% by weight of palladium.

Catalyst C12 was prepared by impregnating a zirconium oxide support (MEL Chemicals) with a solution of H$_2$IrCl$_6$. After impregnation, the solid was dried for 24 h at 120° C. then calcined in a flow of air at a temperature of 500° C. for 4 h. The solid was reduced in a stream of hydrogen at 500° C. for two hours. Catalyst C12 contained 1.1% by weight of iridium.

Example 15: Transformation of Cellulose Using the Catalysts C10, C11, C12 in Combination with Iron Chloride Hexahydrate (in Accordance with the Invention)

This example concerns the conversion of cellulose using a combination of a catalyst C10, C11, C12 described in Example 10 and a metallic salt for the production of mono- and poly-oxygenated products.

50 mL of water, 1.5 g of SigmaCell® cellulose, 0.03 g of iron chloride and catalyst C10, C11 or C12 were introduced into a 100 mL autoclave under an atmosphere of nitrogen. The mass of catalyst was calculated such that the quantity of noble metal introduced was equivalent. The iron chloride hexahydrate metallic salt was soluble in water (T=25° C., P=atmospheric P).

The autoclave was heated to 190° C. and a pressure of 5 MPa of nitrogen was introduced. After 12 h of reaction, the reaction medium was removed and centrifuged. Samples were also taken during the tests and analysed by high pressure liquid chromatography (HPLC) using refractometry in order to determine the quantity of conversion products in the aqueous solution.

The results obtained are shown in Table 6.

TABLE 6

Dissolution of cellulose and formation of humins

| Catalysts | Mass of catalyst | Dissolution at 6 h (%) | Dissolution at 12 h (%) | Formation of humins |
|---|---|---|---|---|
| Sans catalyst | 0 | 50 | 52 | Yes |
| FeCl$_3$ + Pt/ZrO$_2$ (C10) | 0.55 g | 78 | 82 | No humins |
| FeCl$_3$ + Pd/ZrO$_2$ (C11) | 0.27 g | 52 | 62 | No humins |
| FeCl$_3$ + Ir/ZrO$_2$ (C12) | 0.55 g | 61 | 73 | No humins |

Example 16: Preparation of Heterogeneous Catalysts Containing Silicon Oxide and Aluminium A series of catalysts was prepared by impregnating a silica-alumina support.

Catalyst C13 was prepared by impregnating a silica-alumina support (Siralox 30, Sasol) with a solution of hexachloroplatinic acid. After impregnation, the solid was dried for 24 h at 120° C. then calcined in a flow of air at a temperature of 500° C. for 4 h. The solid was reduced in a stream of hydrogen at 500° C. for two hours. Catalyst C13 contained 0.7% by weight of platinum.

Catalyst C14 was prepared by impregnating a silica-alumina support (Siralox 30, Sasol) with a solution of ruthenium acetylacetone, Ru(acac)$_3$, dissolved in acetone. After impregnation, the solid was dried for 24 h at 120° C. then calcined in a flow of air at a temperature of 300° C. for 4 h. The solid was reduced in a stream of hydrogen at 300° C. for two hours. Catalyst C14 contained 1.2% by weight of ruthenium.

Catalyst C15 was prepared by impregnating catalyst C13 with a solution of tin chloride, SnCl$_2$. After impregnation, the solid was dried for 24 h at 120° C. then calcined in a flow of air at a temperature of 550° C. for 4 h. Catalyst C15 contained 0.7% by weight of platinum and 1.5% by weight of tin.

Catalyst C16 was prepared by impregnating a silica-alumina support (Siralox 30, Sasol) with a solution of nickel nitrate. After impregnation, the solid was dried for 24 h at 120° C. then calcined in a flow of air at a temperature of 500° C. for 4 h. The solid was reduced in a stream of hydrogen at 500° C. for two hours. Catalyst C16 contained 3.6% by weight of nickel.

Catalyst C17 was prepared by impregnating catalyst C16 with a solution of tin chloride, SnCl$_2$. After impregnation, the solid was dried for 24 h at 120° C. then calcined in a flow of air at a temperature of 550° C. for 4 h. The solid was reduced in a stream of hydrogen at 500° C. for two hours. Catalyst C17 contained 3.6% by weight of nickel and 1.3% by weight of tin.

Example 17: Transformation of Cellulose Using Catalysts C13, C14, C15, C16 and C17 in Combination with Iron Chloride Hexahydrate (in Accordance with the Invention)

This example concerns the conversion of cellulose using a combination of one or more heterogeneous catalysts selected from C13, C14, C15, C16 and C17 described in Example 12 and a metallic iron chloride salt for the production of mono- and poly-oxygenated products.

50 mL of water, 1.5 g of SigmaCell® cellulose, 0.03 g of iron chloride and catalyst C13, C14, C15, C16 and C17 were introduced into a 100 mL autoclave under an atmosphere of nitrogen. The iron chloride hexahydrate metallic salt was soluble in water (T=25° C., P=atmospheric P).

The autoclave was heated to 185° C. and a pressure of 5 MPa of nitrogen was introduced. After 12 h of reaction, the reaction medium was removed and centrifuged. Samples were also taken during the tests and analysed by high pressure liquid chromatography (HPLC) using refractometry in order to determine the quantity of conversion products in the aqueous solution.

The results obtained are shown in Table 7.

TABLE 7

Dissolution of cellulose and formation of humins

| Heterogeneous catalyst | $m_{catalyst}$ (g) | Dissolution at 6 h (%) | Dissolution at 12 h (%) | Formation of humins |
|---|---|---|---|---|
| $FeCl_3$ + Pt/$SiO_2$—$Al_2O_3$ (C13) | 0.5 | 78 | 98 | No humins |
| $FeCl_3$ + Ru/$SiO_2$—$Al_2O_3$ (C14) | 0.30 | 62 | 82 | No humins |
| $FeCl_3$ + Ni/$SiO_2$—$Al_2O_3$ (C15) | 1.0 | 30 | 45 | No humins |
| $FeCl_3$ + PtSn/$SiO_2$—$Al_2O_3$ (C16) | 1.9 | 70 | 90 | No humins |
| $FeCl_3$ + NiSn/$SiO_2$—$Al_2O_3$ (C17) | 0.9 | 50 | 61 | No humins |
| $FeCl_3$ + Ru/$SiO_2$—$Al_2O_3$ + Pt/$SiO_2$—$Al_2O_3$ (C13 + C14) | 0.30 + 0.09 | 68 | 86 | No humins |

Example 18: Transformation of Cellulose Using Catalyst C1 in Combination with Iron Chloride Hexahydrate (in Accordance with the Invention) Under Variable Operating Conditions This example concerns the conversion of cellulose using a combination of a heterogeneous catalyst C and a metallic iron chloride salt for the production of mono- and poly-oxygenated products.

50 mL of water, 1.5 g of SigmaCell® cellulose, 0.03 g of iron chloride and 0.5 g of catalyst C1 were introduced into a 100 mL autoclave under an atmosphere of nitrogen. The iron chloride hexahydrate metallic salt was soluble in water (T=25° C., P=atmospheric P).

The autoclave was heated to a temperature T in the range 150° C. to 250° C. and a pressure P of hydrogen varying between 5 MPa and 8 MPa was introduced. After 12 h of reaction, the reaction medium was removed and centrifuged. Samples were also taken during the tests and analysed by high pressure liquid chromatography (HPLC) using refractometry in order to determine the quantity of conversion products in the aqueous solution.

The results obtained are shown in Table 8.

TABLE 8

Dissolution of cellulose and formation of humins

| Temperature (° C.) | Pressure (MPa) | Dissolution at 6 h (%) | Dissolution at 12 h (%) | Formation of humins |
|---|---|---|---|---|
| 150 | 0.50 | 10 | 11 | No humins |
| 170 | 0.50 | 18 | 22 | No humins |

TABLE 8-continued

Dissolution of cellulose and formation of humins

| Temperature (° C.) | Pressure (MPa) | Dissolution at 6 h (%) | Dissolution at 12 h (%) | Formation of humins |
|---|---|---|---|---|
| 190 | 0.50 | 72 | 85 | No humins |
| 190 | 0.80 | 75 | 91 | No humins |
| 210 | 0.50 | 76 | 95 | No humins |
| 245 | 0.50 | 72 | 60 | No humins |

Example 19: Transformation of Glucose Using Catalyst C1 (0.5% by Weight Pt/$ZrO_2$—$WO_x$) in Combination with a Homogeneous Catalyst (in Accordance with the Invention)

This example concerns the conversion of glucose using a combination of catalyst C1 described in Example 1 and a metallic salt for the production of mono- and poly-oxygenated products.

50 mL of water, 1.3 g of glucose, a metallic salt and 0.55 g of catalyst C1 were introduced into a 100 mL autoclave under an atmosphere of nitrogen. The metallic salts were soluble in water (T=25° C., P=atmospheric P). The mass of metallic salt added was described in Table 2.

The autoclave was heated to 190° C. and a pressure of 5 MPa of nitrogen was introduced. After 12 h of reaction, the reaction medium was removed and centrifuged. Samples were also taken during the tests and analysed by high pressure liquid chromatography (HPLC) using refractometry in order to determine the quantity of conversion products in the aqueous solution.

The results obtained are shown in Table 9.

TABLE 9

Transformation of glucose and formation of humins

| Metallic salt | Mass of metallic salt (g) | Conversion at 6 h (%) | Conversion at 12 h (%) | Formation of humins |
|---|---|---|---|---|
| Pt/ZrW (C1) + $FeCl_3$ | 0.033 | 72 | 100 | No humins |

The invention claimed is:

1. A process for the transformation of lignocellulosic biomass or cellulose into mono- or poly-oxygenated compounds, in which the lignocellulosic biomass or the cellulose is brought into simultaneous contact with a combination of one or more homogeneous catalysts and one or more heterogeneous catalysts in the same reaction chamber, in the presence of at least one solvent, said solvent being water alone or as a mixture with at least one other solvent, in a reducing atmosphere, and at a temperature in the range 80° C. to 250° C. and at a pressure in the range 0.5 MPa to 20 MPa, said homogeneous catalyst or catalysts comprising a metallic salt which may or may not be hydrated with general formula $MX_n.n'H_2O$ in which M is a metal from groups 3 to 16 of the periodic classification, n is a whole number in the range of from 1 to 6 and n' is a whole number in the range of from 0 to 6 and X is at least one anion selected from the group consisting of halides, nitrates, carboxylates, halocarboxylates, acetylacetonates, alcoholates, phenolates, which may or may not be substituted, sulphates, alkylsulphates, phosphates, alkylphosphates, halosulphonates, alkylsulphonates, perhaloalkylsulphonates, bis(perhaloalkylsulphonyl)amides, and arenesulphonates, which may or may not be substituted with halogen or haloalkyl groups, said anions X possibly being identical or different in the case in which n is greater than 1, said heterogeneous catalyst or catalysts comprising at least one metal from groups 6 to 11 or group 14 of the periodic classification and a support, wherein said support is an oxide of aluminium, titanium, silicon, zirconium, cerium or niobium, or mixed oxides of zinc, copper or cobalt aluminates, said oxides being doped or not doped with at least one metallic compound selected from the group consisting of tungsten, tin, molybdenum and antimony, used alone or as a mixture, crystalline or non-crystalline aluminosilicates, aluminophosphates and amorphous or crystalline carbon compounds.

2. The process according to claim 1, in which the metal M of the homogeneous catalyst or catalysts is selected from the group consisting of Cr, Mn, Fe, Co, Ni, Cu, Zn, Al, Ga, In, Cu, Zr, Bi, La and Sn.

3. The process according to claim 1, in which the metal M of the homogeneous catalyst or catalysts is selected from the group consisting of Cr, Mn, Fe, Zn, Al, Sn, Cu, Zr, Bi and La.

4. The process according to claim 1, in which the anion X of the homogeneous catalysts is at least one anion selected from the group consisting of halides, alkylsulphonates, perhaloalkylsulphonates, and bis(perhaloalkylsulphonyl) amides.

5. The process according to claim 4, wherein when n is equal to 3, the anion X of the homogeneous catalyst or catalysts is a chloride.

6. The process according to claim 1, wherein the group 6 to 11 metals are selected from the group consisting of Mo, W, Re, Ru, Co, Rh, Ir, Ni, Pd, Pt, Cu, and the group 14 metal is Sn, wherein said metals are provided alone or as a mixture.

7. The process according to claim 6, in which the metal of the heterogeneous catalyst or catalysts is platinum.

8. The process according to claim 1, in which the quantity of metal on said heterogeneous catalyst or catalysts is in the range of from 0.01% to 10% by weight with respect to the total mass of said catalyst or catalysts.

9. The process according to claim 1, in which the homogeneous catalyst or catalysts are introduced into the reaction chamber in a quantity corresponding to a biomass/homogeneous catalyst(s) ratio in the range of from 1 to 1000 by weight.

10. The process according to claim 1 wherein when said process is operated in the presence of water mixed with at least one other solvent, the mixture of solvents comprises a quantity by weight of water of more than 5 by weight with respect to the total mass of said mixture.

11. The process according to claim 1, in which said process is operated in the presence of water alone.

12. The process according to claim 1, in which the process operates in the presence of at least one solvent with the exception of ionic liquid solvents.

13. The process according to claim 1, in which the reducing atmosphere is an atmosphere of hydrogen, pure or as a mixture.

14. The process according to claim 1, operated at a temperature in the range of from 150° C. to 240° C., and at a pressure in the range of from 2 MPa to 10 MPa.

15. The process according to claim 10, wherein the mixture of solvents comprises a quantity by weight of water of more than 30% by weight.

16. The process according to claim 10, wherein the mixture of solvents comprises a quantity by weight of water of more than 50%.

* * * * *